United States Patent [19]

Ansell

[11] Patent Number: 5,183,664
[45] Date of Patent: Feb. 2, 1993

[54] THIN FILM ADHESIVE DRESSINGS PREPARATION AND USE

[75] Inventor: Christopher W. G. Ansell, Sawston, United Kingdom

[73] Assignee: Smith and Nephew Associated Companies p.l.c., United Kingdom

[21] Appl. No.: 632,055

[22] Filed: Dec. 21, 1990

Related U.S. Application Data

[63] Continuation of Ser. No. 339,134, Apr. 17, 1989, abandoned, which is a continuation of Ser. No. 146,778, Dec. 21, 1987, abandoned.

[30] Foreign Application Priority Data

Sep. 20, 1986 [GB] United Kingdom ............ 8622695
Dec. 6, 1986 [GB] United Kingdom ............ 8629231
Jan. 16, 1987 [GB] United Kingdom ............ 8700943
Jan. 16, 1987 [GB] United Kingdom ............ 8700944
Jan. 22, 1987 [GB] United Kingdom ............. 871434
Sep. 21, 1987 [WO] PCT Int'l Appl. ... PCT/GB87.00657

[51] Int. Cl.$^5$ ............................................ A61L 15/16
[52] U.S. Cl. .................................. 424/445; 424/443; 424/448; 128/849
[58] Field of Search ...................... 424/543, 445, 448

[56] References Cited

U.S. PATENT DOCUMENTS 4,661,499  4/1987  von Bittera ..................... 428/211

Primary Examiner—Paul R. Michl
Assistant Examiner—Leon R. Horne
Attorney, Agent, or Firm—Rosenman & Colin

[57] ABSTRACT

Thin film adhesive dressings comprise a support layer having a continuous coating on one side thereof of a gel adhesive. The adhesive is non self-adherent and preferably comprises a hydrophilic gel containing polyurethane residues. The dressings may be highly water absorbent and are moisture vapor permeable, having a moisture vapor transmission rate of not less than 300 gm m$^2$ hr$^{-1}$ at a relative humidity difference of 10 to 100% when in contact with moisture vapor.

30 Claims, No Drawings

THIN FILM ADHESIVE DRESSINGS PREPARATION AND USE

CROSS-REFERENCE this is a division of Ser. No. 339,134 filed Apr. 17, 1989 abandoned which is a continuation of Ser. No. 146,778 filed Dec. 21, 1987 abandoned.

This invention relates to thin film adhesive dressings such as those suitable for use on exuding and non-exuding wounds, or for use as an incise drape or for covering and securing cannulae in place at intravenous access sites. More particularly the invention relates to moisture vapour permeable dressings.

Moisture vapour permeable thin films coated with adhesive and which are suitable for application to the skin have been disclosed in for example British Patent No. 1280631 and in U.S. Pat. No. 3645835, European Patent Applications Nos 51935, 81987, 117632, 178740 and U.S. Pat. Nos 4372303, 4374520, 4413621, like. The known dressings of this type in commercial use have proved useful because the microscopically continuous nature of the adhesive layer and the film prevent ingress of bacteria into the wound.

These dressings have the added advantage that they do not cause maceration of healthy skin to which they may be applied because both the film and adhesive layer are moisture vapour permeable and generally provide the dressing with a moisture vapour transmission rate (MVTR) of between 300 and 800 g/m²/24 hr at 37° C. and 100% to 10% relative humidity difference.

However, a disadvantage which may arise with known incises drapes, for example, is that if the patient sweats profusely the adhesive may be affected and the drape may lift away from the skin and thereby may compromise the sterility of the operation site.

Similarly with commercially available intravenous access site dressings (I.V. dressings), although the adhesives employed are moisture vapour permeable, the MVTR of the adhesive when present as a continuous film is not sufficiently high to permit rapid evaporation of moisture through a dressing which has been applied to an exuding site. The result of using such an adhesive can be to cause the formation of a moist area which can predispose to bacterial growth.

Thin film dressings known for use as wound dressings also suffer from the disadvantage that although the adhesives employed are moisture vapour permeable, the MVTR of the adhesive when present as a continuous film is not sufficiently high to permit rapid evaporation of moisture from a dressing which has been applied to an exuding wound. The result of using such an adhesive can be to cause the formation of an unsightly blister which can predispose to leakage and so lead to bacterial contamination.

One method of overcoming the disadvantages associated with known thin film dressings is to provide the adhesive layer as a macroscopically discontinuous layer in the form of a porous or a pattern spread layer (see for example European Patent No. 91800). Such a layer is coated onto a continuous moisture vapour permeable or water absorbent backing layer so that the dressing remains bacteria-proof while also possessing a high moisture vapour transmission rate. However, the discontinuous nature of the adhesive layer can give rise to other disadvantages. The edges of the dressing may lift at the adhesive free areas. The discontinuous adhesive layer may allow exudate, in the case of wound or IV dressings to spread away from the wound or access site over the skin which may cause trauma to the skin. The exudate may ultimately reach the edge of the dressing thereby providing a possible route by which bacteria might reach the wound or site. A discontinuous adhesive layer may allow local drying out of the wound and hence to scab formation. Neither of these occurences are conducive to wound healing nor to atraumatic removal of the dressing.

It would be advantageous therefore if a dressing could be provided with an adhesive present as a continuous layer whereby the above disadvantages of grossly discontinuous adhesive layers could be avoided. It would also be advantageous if the dressing had a greater moisture vapour transmission rate when the adhesive layer was in contact with water than when the adhesive layer was in contact with moisture vapour and not water. This property has been shown to be an advantage in dressings in which the adhesive is grossly discontinuous as such dressings may be used on both exuding and non-exuding wounds to advantage. This property has not previously been observed in a dressing with a continuous adhesive layer. It would be a further advantage if the adhesive had little or no propensity to cause irritation even after prolonged contact with the skin.

A further disadvantage which has been observed to occur with adhesive thin film dressings is that if the dressing becomes creased and/or two parts of the adhesive surface adhere together, it has proved almost impossible to separate them again to provide a flat dressing and so the dressing must be discarded. It is an advantage of the adhesive used in the dressings of the present invention that it is non self adherent and so it can be easily peeled from itself should two surfaces come into contact. This is manifest by the adhesive having a low peel strength when peeled from a steel surface.

British Patent No. 1379312 discloses pressure sensitive polyurethane adhesives and adhesive coated substrates which have high peel adhesion and are used in industrial applications. The adhesives are said to adhere strongly to substrates and are difficult to remove. The adhesives would not be suitable for medical use and such use is not disclosed or suggested.

British Patents Nos. 1351909 and 1468617 disclose polyurethane adhesive coated tapes for releasing medicament to the skin. However, these polyurethane adhesives have a low crosslink density and may be susceptible to self-adhesion of the type avoided by the adhesives used in the present invention.

Accordingly, the present invention provides a thin film dressing which comprises a backing layer having over one surface thereof a continuous adhesive layer, which adhesive comprises a cross-linked gel adhesive which is not self-adherent and which may be removed from the skin without damage thereto, and wherein the dressing has a moisture vapour transmission rate of at least 300 $gm^{-2} hr^{-1}$ at 37° C. and at a relative humidity difference of from 10 to 100% when in contact with moisture vapour.

Preferred gel adhesives are those based upon polyurethane gels.

Suitably the adhesive is a pressure sensitive adhesive.

By continuous layer of adhesive it is meant that the adhesive layer covers the surface to which it is applied without visible gaps. Thus this continuous layer may contain micropores although preferably the layer is microscopically continuous.

The backing layer and the adhesive layer may be such as to allow for visual inspection of the wound through the dressing when the dressing is in place. The backing layer and the adhesive layer are aptly together translucent but preferably both will be transparent.

The preferred dressings of the present invention exhibit different moisture vapour transmission rates depending upon whether the adhesive layer of the dressing is in contact with moisture vapour or with water.

The moisture vapour transmission rate when the adhesive is in contact with moisture vapour but not water is referred to herein after as the upright moisture vapour transmission rate (upright MVTR) and may be measured by the method described hereinafter. Suitably the upright MVTR of the dressing will not be greater than 2000 gm$^{-2}$ 24h$^{-1}$ at 37° C. and 100% to 10% relative humidity difference. A dressing having an upright MVTR below this value generally allows the wound to remain in a moist condition even in the absence of exudate. More suitably the upright MVTR will not be greater than 1800 gm$^{-2}$ 24h$^{-1}$ and preferably will not be greater than 1600 gm$^{-2}$ 24h$^{-1}$. However, the upright moisture vapour transmission rate of the backing layer is advantageously greater than 500 gm$^{-2}$ 24h$^{-1}$, as it has been found that as the adhesive layer absorbs water, the adhesive layer and a backing layer of MVTR of below 300 gm$^{-2}$ 24h$^{-1}$ tend to delaminate. Thus suitably the dressings of the present invention will have an upright MVTR of greater than 600 gm$^{-2}$ 24h$^{-1}$ at 37° C. and 100% to 10% relative humidity difference, more suitably more than 1000 gm$^{-2}$ 24h$^{-1}$, most suitably more than 1200 gm$^{-2}$ 24h$^{-1}$ and preferably will have an upright MVTR of between 1400 gm$^{-2}$ 24h$^{-1}$ and 1600 gm$^{-2}$ 24h$^{-1}$ under the conditions specified above.

The moisture vapour transmission rate when the adhesive is in contact with water but not moisture vapour referred to herein after as the inverted moisture vapour transmission rate (inverted MVTR) and may be measured by the method described hereinafter. Suitably the dressing of the present invention will have an inverted MVTR of greater than 5000 gm$^{-2}$ 24h$^{-1}$ at 37° C. and 100% to 10% relative humidity difference, more suitably may have an inverted MVTR of greater than 7000 gm$^{-2}$ 24h$^{-1}$, most suitably greater than 9000 gm$^{-2}$ 24h$^{-1}$ and preferably greater than 12,000 gm$^{-2}$ 24h$^{-1}$ at 37° C.

In their preferred form, the gel adhesives employed for the dressings of the invention are water soluble thereby making it possible to provide adhesive dressings which are conformable to the wound or body surface, which permit rapid evaporation of exudate from exuding wounds while preventing dehydration of the wound even when exudation has ceased so providing a moist environment for improved wound healing. The adhesive dressings may also protect the wound or access site from mechanical trauma and can serve as a carrier for topically applied pharmacologically active agents or medicaments such as antibacterial and antimicrobial agents. The dressings may remain in place over a wound for a period of days yet the dressings may be removed without causing unacceptable discomfort or compromising the healing wound. Even on non-exuding wounds, the environment at or near the wound is maintained in a moist condition which is conducive to wound healing.

Suitably the pressure sensitive adhesive will be a water absorbent gel adhesives. Typically the adhesive can have a water content when hydrated of from 5 to 95% by weight of water and preferably 35 to 90% by weight of water.

Preferred thin film dressings comprises a backing layer having over one surface thereof a continuous layer of pressure sensitive gel adhesive capable of containing from 35 to 95% by weight of water when hydrated which dressing has a moisture vapour transmission rate of not greater than 2000 gm$^{-2}$ 24hr$^{-1}$ at 37° C. and 100% to 10% relative humidity difference when the adhesive is in contact with moisture vapour and a moisture vapour transmission rate of not less than 5000 gm$^{-2}$ 24hr$^{-1}$ at 37° C. and 100% to 10% relative humidity difference when the adhesive is in contact with water.

Aptly the adhesive is a polyurethane which contains from 35 to 90% by weight of water when hydrated and preferably 50 to 75% by weight of water when hydrated.

Another suitable pressure sensitive gel adhesive is a polyurethane which contains acrylate residues and which contains from 70 to 90% by weight of water when hydrated and more aptly 75 to 88% by weight of water when hydrated and preferably 80 to 85% by weight of water when hydrated.

The water absorption of the adhesive can be obtained by taking a known weight of the dry adhesive (D) and immersing in water for 24 hours The hydrated polymer is removed from the water, surface water is removed by lightly blotting with absorbent paper and then the weight of the hydrated adhesive (W) taken. The water absorption of the adhesive (% by weight) can then be calculated as (W-D) x 100/W.

The gel adhesives employed for the dressings of the invention will suitably have a content of materials leachable in to water of below 10% by weight more suitably will be below 5% and preferably below 2.5% of materials leachable into water The adhesives used in these dressings do not require the presence of additives such as humectants and plasticisers which may leach out into a wound surface which is generally considered to be unsatisfactory.

The adhesive layer employed in the dressings of the invention may vary in thickness depending on the type of application for which the dressings is required If the dressing is applied to a wound which is generating a large amount of exudate then the absorptive properties of the adhesive layer may be utilised and a thick layer of adhesive may be used. Suitably the thickness of the adhesive for use on exuding wounds may be from 0.5 to 5 mm, more suitably may be 0.75 mm to 4 mm, most suitably 1 to 3.5 mm and preferably 2 to 3 mm.

For use on wounds which are generating small amounts of or no exudate a thin layer of adhesive may suffice. Suitably the thickness of the adhesive for use on non-exuding wounds may be from 10 to 100 μm, more suitably from 30 to 50 μm and preferably of from 35 to 45 μm.

In order to take advantage of the absorptive properties of the material forming the adhesive layer, the adhesive layer used is usually substantially thicker than that used on incise drapes and I.V. dressings. It is surprising that even when used as the thick layer, the adhesive does not deliteriously effect the upright and inverted MVTRs of the dressing.

For IV applications the adhesive layer will suitably have thickness of from 10 to 100 μm, more suitably from 20 to 70 μm, most suitably from 30 to 50 μm and preferably from 35 to 45 μm. When used for incise drapes the adhesive layer of the dressing can be a thickness of from 10 to 150 μm, more suitably from 10 to 75 μm, most suitably from 30 to 50μm and preferably from 35 to 45 μm.

The backing layer may be formed from any moisture vapour permeable filmic material suitably having an MVTR of greater than 500 $gm^{-2} 24h^{-1}$. Suitable materials include microporous films, films of hydrophilic polymers such as polyurethanes, polyether polyesters, polyether polyamides, cellulosics and the like. Preferably the backing layer is a transparent film. The adhesive layer is applied to such backing layers as a continuous layer thereby helping to maintain the bacteria proof and liquid water impermeability of the dressing.

A favoured backing layer is formed from a hydrophilic polyurethane. Suitable hydrophilic polyurethanes include those having the composition and prepared by the process described in British Patent No. 2093190B. Favoured hydrophilic polyurethanes are those which contain from 5 to 50% by wEight of water when hydrated more suitably 10 to 40% by weight of water and which have a thickness when present in a dressing of from 10 to 80 μm, more suitably 20 to 45 μm. A preferred film of hydrophilic polyurethane has a water content when hydrated of 20 to 30% for example 25% amd a thickness of 20 to 45 μm, for example 30 μm.

In a preferred aspect therefore the present invention provides a wound dressing which comprises a backing material comprising a hydrophilic polyurethane which has a water content when hydrated of 10 to 40% and a thickness of from 15 to 80 μm having over one surface thereof a continuous layer of pressure sensitive adhesive comprising a polyurethane which contains from 70 to 90% by weight of water when hydrated and having a thickness of from 0.5 to 5 mm which dressing has a moisture vapour transmission rate of between 1400 and 1600 $gm^{-2} 24h^{-1}$ at 37° C. and 100 to 10% relative humidity difference when the adhesive is in contact with moisture vapour and a moisture vapour transmission rate of greater than 7000 $gm^{-1} 24h^{-1}$ at 37° C. when the adhesive is in contact with water.

In another preferred aspect the present invention provides a surgical incise drape which comprises a backing layer having over a surface thereof a continuous layer of pressure sensitive adhesive capable of containing from 35 to 95% by weight of water when hydrated which drape has a moisture vapour transmission rate of greater than 800 $gm^{-2} 24 h^{-1}$ at 37° C. and 100% to 10% relative humidity difference when the adhesive is in contact with moisture vapour and a moisture vapour transmission rate of greater than 2500 $gm^{-2} 24 h^{-1}$ at 37° C. when the adhesive is in contact with water.

A particularly favoured type of material for forming the backing layer for dressings used as incise drapes comprises a polymer which in contact with water has a greater moisture vapour transmission rate than when in contact with moisture vapour but not water so that when used in the drape the drape shows a similar effect. The use of this type of backing layer with a continuous adhesive layer has not previously been known and there is provided a drape of particularly desirable properties.

The material which forms the backing layer should be such that when coated with a continuous layer of the water absorbent pressure sensitive adhesive the combination will have a moisture vapour transmission rate of above 800 $gm^{-2} 24 h^{-1}$ at 37° C. and 100% to 10% relative humidity difference, more suitably more than 1200 $gm^{-2} 24 h^{-1}$ and preferably from 1400 to 2000 $gm^{-2} 24 h^{-1}$ when the adhesive is in contact with moisture vapour.

The material which forms the backing layer should provide the drape with an inverted moisture vapour transmission rate of greater than 2500 $gm^{-2} 24 h^{-1}$ at 37° C. more suitably in the range from 3000 to 18000 $gm^{-2} 24 h^{-1}$ and preferably from 5000 to 12000 $gm^{-2} 24 h^{-1}$.

Suitably the adhesive may contain a medicament such as an antibacterial agent.

Suitable antibacterial agents include chlorhexidine and salts thereof, iodophors such as polyvinyl pyrrolidone-iodine, silver salts such as silver sulphadiazine, polymeric biguanides for example those antibacterial agents known as Vantocil (Trade mark) and metronidazole and compatible mixtures thereof. Suitably the adhesive will contain from 0.1 to 10% by weight of the adhesive of the antibacterial agent. The antibacterial agent may be dissolved in the adhesive or may be dispersed as a separate phase such as a solid in the adhesive or may be in localised areas such as near the skin contacting surface of the adhesive.

The dressings of the present invention may be prepared by taking the material which is to form the backing layer and bringing it into contact with a film of the adhesive at the required thickness preferably without the use of any further adhesives for example by normal laminating techniques such as passing between the nip of two rollers under pressure.

Normally the dressings are presented for use with a silicone release paper (or other convenient material known in the art) to cover and protect the adhesive. This protector is removed prior to use. The dressings may also be provided with a support layer or handles or the like attached to the non-adhesive side of the transparent film or at the edges of the film. The support layer is preferably removable after application of the dressing. Naturally neither protector nor support layer are essential features of the dressing since neither perform any function when the dressing is in use. Suitable forms of removable protectors support layers and handles for use with the wound dressings of the present invention include those described in for example European Patent Applications No. 51935, 81987, 81989, 18990, 117632, 120570, 189999 and 161865, United Kingdom Application No. 2120104, United Kingdom Patent No. 1280631 and U.S. Pat. Nos. 4372303 and 4374520. A particularly apt support layer is described in European Patent Application No. 51935 and illustrated in FIGS. 1 and 2 of that application and a particularly apt system of handles is described in European Patent Application No. 161865.

The dressings according to the invention may be, and are usually, provided in sterile form and may be packaged in a bacteria-proof and waterproof pack or pouch. Sterilisation may be achieved in a conventional manner for example by the use of gamma irradiation, heat or ethylene oxide gas.

In use the sterile dressing is removed from the pouch, the protector removed from the adhesive surface of the dressing and the dressing is placed over the wound or site and adhered to the skin surrounding the wound.

In a further aspect therefore the present invention provides a method of treating a wound on an animal body by applying to the wound an adhesive dressing as hereinbefore described.

Wound dressings in accordance with the present invention may be used to treat cavernous wounds such as leg ulcers, skin ulcers, decubitus ulcers and the like which may emit unusually large volumes of exudate. The wound cavity is first filled with an absorbent filling material before covering with the dressing. Suitable filling materials include collagen gels, polymeric gels such as salts of hydrolised acrylonitrile starch-graft copolymers see for example U.S. Pat. No. 4226232, United Kingdom Patents Nos 2043668 and 2124487, polysaccharide-polyacrylamide copolymers, granular absorbents such as alginate salts, cross-linked dextran and dextrin see for example British Patent Nos 1454055, 1472659. The filling material absorbs wound exudate which reduces the risk of blister formation and leakage beneath the dressing when an unusually large amount of wound exdate is produced. It is believed that the low upright MVTR of the dressing prevents the absorbent filling material from drying out and hence adhering to the granulating wound bed. When changing the dressing, the wound dressing is removed and the filling material flushed from the wound using for example sterile saline solution.

In another aspect therefore present the invention provides a method of treating a cavernous wound which comprises filling into the wound cavity an absorbent filling material and covering with a dressing as hereinbefore described.

In use as an IV dressing the sterile dressing is removed from the pouch, the protector removed from the adhesive surface of the dressing and the dressing is placed over the injection site and adhered to the skin and over the cannula.

In a further aspect the present invention provides a method of retaining a cannula on the skin at a cannula site which method comprises covering the site with a transparent film having upon substantially the whole of one surface thereof a continuous layer of transparent adhesive comprising an inherently tacky polyurethane gel which adhesive is not self-adherent and which may be removed from the skin without causing damage thereto.

When employed as incise drapes thin film dressings in accordance with the present invention may be prepared by forming a film of the adhesive at the required thickness and contacting it with the backing film to form a laminate. A release coated protector may be placed over the adhesive layer and the laminate cut to a size suitable for use as an incise drape for example 10 $\times$ 20 cm. 20$\times$20 cm, 20$\times$40 cm, 40$\times$80 cm or the like. The incise drape may be packaged in a bacteria-proof and water-proof pouch and be sterilized by conventional methods such as irradiation and ethylene oxide.

In use the sterile incise drape is removed from the pouch, the protector removed from the adhesive surface and the drape is adhered to the skin.

A suitable method of determining the upright moisture vapour transmission rate of the dressing of this invention is as follows Discs of material under test are clamped over Payne Permeability Cups (flanged metal cups) using sealing rings and screw clamps. The exposed surface area of the test sample may be conveniently 10 cm$^2$. Each cup contains approximately 10 ml of distilled water After weighing the cups are placed in a fan assisted electric oven maintained at 37$\pm$1° C. The relative humidity within the oven is maintained at 10% by placing 1 Kg of anhydrous 3-8 mesh calcium chloride on the floor of the oven. The cups are removed after 24 hours, allowed to cool for 20 minutes and reweighed. The MVTR of the test material is calculated from the weight loss expressed in units of grams of weight per square meter per 24 hours.

A suitable method of determining the inverted moisture vapour transmission rate of the dressing of this invention is as follows. The method described above is employed except that the Payne Cups are inverted in the oven so that the water within the cups is in contact with the test material and in this case with the adhesive.

Polyurethane gel adhesives useful for the dressings of the present invention may be prepared by reacting isocyanate prepolymer, which is itself the reaction product of polyfunctional isocyanate and polyoxyalkylene diol monoalkyl ether, with acrylate comprising hydroxyl-containing ester of acrylic or methacrylic acid and other hydroxyl containing compounds whereby the proportion of the acrylate is such that it will react from 15 to 25% of the free isocyanate groups in the prepolymer with the other hydroxyl-containing compound reacting with the remainder and cross-linking the polymer formed by means of irradiation. Alternatively the polyurethane gel adhesive may be produced by reacting the isocyanates prepolymer with molar excess of water or with a stoichiometric amount of a polyol or polyol mixture.

Suitable polyoxylalkylene diol mono alkyl ethers for use in forming the prepolymers and polymers employed to prepare adhesives for the dressings of the present invention include those-in which alkyl group contains from 1 to 18 carbon atoms and more on suitably 2 to 12 carbon atoms and preferably 2 to 6 carbon atoms for example 4 carbon atoms that is the mono alkyl is a monobutyl ether.

Suitably the polyoxyalkylene residue in the mono alkyl ether is a hydrophilic residue that contains polyoxyethylene or polyoxypropylene residues or mixtures thereof. Preferred polyoxyalkylene residues are those which contain a mixture of polyoxyethylene and polyoxypropylene residues in a ratio of from 20:80 to 80:20 for example 50:50 and in which residues are random arranged with respect to each other.

A referred polyoxyalkylene diol mono alkyl ether is therefore polyoxyethylene - polyoxypropylene mono butyl ether in which the ratio of polyoxyethylene to polyoxypropylene residues is 50:50 such as those sold under the trade name Emkarox polyols available from I.C.I plc.

Aptly the molecular weight of the monoalkyl ether is from 3000 to 12000, and more suitably is 4000 to 10000 and preferably is 5000 to 9000 It has been found that polyoxyalkylene diol monoalkyl ethers within this molecular weight range provide polymers which are tacky and suitable for use on the skin while use of lower molecular weight materials tend to provide polymers which are not suitable for use as adhesives because they are insufficient tacky.

The polyoxyalkylene diol mono alkyl ethers for use in forming the prepolymer or polymer will normally contain water. It is preferred however that the polyoxyalkylene diol in monoalkyl ether contains less than 1% by weight of water so as to limit the proportion of urea groups formed in the reaction with the polyisocyanate.

The polyisocyanate used for forming the prepolymer will have a functionality of greater than 2 and may suitably have a functionality of from 2.1 to 5 and more suitably from 2.2 to 3.5 and preferably from 2.5 to 3.0 for example 2 5, 2.7, 2.85 or 2.9. Suitably polyisocyanates include (cyclo) aliphatic and aromatic polyisocyanates. Preferred polyisocyanates are aromatic polyisocyanates for example those based on a polymeric methylene di phenyl diisocyanate, for example the Suprasecs (trade mark), which are available from I.C.I. It is preferred that the functionality of the isocyanate is not more than 3 as this leads to a higher cross-link density and is manifest ultimately as a harder adhesive which may not be advantageous for an adhesive which is to be applied to the skin.

The prepolymers may be simply prepared by heating the two components together in the required proportions at an elevated temperature for sufficient time for the reaction to be completed, for example 90° C. for 2 hours, in the presence of a conventional polyurethane polymerisation catalyst such as 0.2% w/w of dibutyl tin dilaurate (T12). The mole ratio NCO/OH is suitably from 2.0 to 4.0 in this reaction and the prepolymer so formed contains from 1.5 to 3.0% by weight of free-isocyanate groups.

The adhesives used in the present invention may be prepared by reacting the prepolymer described above with hydroxy-containing compounds a proportion of which also contains an unsaturated functionality which is reactive when exposed to irradiation for example ultra violet or electron beam irradiation.

Suitable unsaturated compounds include esters of acrylic of methacrylic acid in which there is at least one hydroxyl functional group which is capable of reacting with isocyanate present Preferred esters include hydroxy ethyl methacrylate and methacrylate mono-esters of polyoxylalkylene diols in which the number of repeating ether units is from 1 to 25 and preferably 2 to 10 for example 6.

The remainder of the hydroxyl-containing compounds may comprise polyols such as diols or triols or mono-ols such as primary alcohols or polyoxyalkylene monoalkyl ethers as hereinbefore described. Preferably the hydroxyl-containing compounds are mono-ols such as polyoxyalkylene monoalkyl ethers or a mono-ol with tackifier properties such as hydroabietyl alcohol.

The proportion of hydroxyl-containing compounds which also contains an unsaturated functionality is such as to react with from 15 to 25% of the free isocyanate groups in the prepolymer The remainder of the free isocyanate groups react with the other hydroxyl-containing compounds defined above.

The resulting polymer has therefore pendant unsaturated groups which are capable of interacting with each other to cross-link the polymer under the influence of a polymerisation initiator and irradiation. One suitable form of radiation is ultraviolet irradiation. The polymer may be mixed with a photoinitiator and the mixture irradiated by means of ultraviolet radiation. This causes the polymer to become cross-linked. The polyurethane polymer so formed is a cross-linked polymer which is capable of absorbing from 35 to 95% by weight of water depending upon the reactants employed.

Alternatively the adhesive may be formed as a 'wet' adhesive by dispersing the uncross-linked polymer and photoinitiator in an appropriate volume of water and the irradiating to form the adhesive. Suitably the wet adhesive may contain from 40 to 65% by weight of water.

In an alternative embodiment polyurethane adhesives may be formed by mixing a prepolymer formed as the reaction product of polyisocyanate and polyoxyalkylene diol mono alkyl ether with a molar excess of water or with a stoichiometric amount of polyol or polyol mixture. The polyol is preferably a diol or mixture of diols. The excess of water used is absorbed by the adhesive produced. Suitable polyoxyalkylene diol mono alkyl ethers for use in forming the prepolymers employed to prepare the adhesives include those as herein before described. The polyisocyanate used for foming the prepolymer will have a functionality of greater than 2 and include those which have been described herein before.

The prepolymers may be simply prepared by heating the two components together in the required proportions at an elevated temperature for sufficient time for the reaction to be completed, for example 90° C. for 2 hours, in the presence of 0.2% w/w catalyst of dibutyl tin dilaurate (T12). The mole ratio NCO/OH is suitable from 2.0 to 4.0 in this reaction.

The adhesives may be prepared by reacting the prepolymer described above with water. The reaction mixture may contain from 10% w/w water and 90% w/w prepolymer to 90% w/w water and 10% w/w prepolymer. It is preferred, however, when forming a tacky film that the concentration of prepolymer is less than 25% w/w. If the concentration of prepolymer is greater than 25% w/w then a tacky foam is produced. Normally the reactants are mixed together at room temperature and allowed to cure for at least 30 minutes. The excess water is taken up into the tacky film or foam to produce a swollen film or foam. It has been found that these films and foams may take up a further amount of water often upto a weight equal to their original weight.

The adhesives may also be prepared by reacting the prepolymer with a stoichometric amount of polyol or mixture of a polyol and a tackifying mono-ol. The reactants are mixed together and cured at elevated temperature for 15 minutes to 2 hours. The resultant polyurethane polymer is in the form of a dry adhesive choice of the polyol and isocyanate-content of the prepolymer govern the degree of tackiness of the resulting adhesive. Thus the lower isocyanate-content of the prepolymer, the lower is the cross-link density adhesive. Thus, also the higher the molecular weight of the polyol the softer is the adhesive mass.

A tackifying mono-ol may be added to the polyol in an amount of 1 to 5% by weight of the polyol and preferably 2 to 3% by weight of the polyol. Suitable mono-ols include hydrogenated abietyl alcohol.

Suitable polyols are diols which include alkylene glycols, di-alkylene glycols and polyoxyalkylene diol block copolymers. Suitable diols include diethylene glycol, polyoxyethylene diol having a molecular weight of about 200 and a polyoxyethylene-polyoxypropylene diol block copolymer diol of molecular wt about 2000.

EXAMPLE 1

A film of a hydrophilic polyurethane (Example 2 of United Kingdom Patent No. 2093190B) having a weight per unit areas of 42 gsm, was laminated a film of the pressure sensitive adhesive having a weight per unit area of 70 gsm. The adhesive was cast as a film onto a silicone coated release paper. In this case both the adhesive layer and the polyurethane film were transparent so that when the release paper was removed and the dressing adhered to the skin the wound IV access site, or surgical site and underlaying skin surface could be seen.

The resulting laminate is cut into pieces of sizes suitable for use on wound dressing, IV dressing or surgical drapes. Pieces which have an adhesive area of 10 cm ×10 cm which are suitable for use as wound dressings or IV dressings whereas larger pieces e.g. 10 cm ×20 cm are suitable for use as surgical drapes. The pieces may be packed and sealed in bacteria-proof and water proof pouches and sterilised by irradiation.

In use the dressing is removed from the pouch, the silicone coated release paper removed and the dressing is placed over the wound or site and is then adhered to the skin surrounding the wound or site. The wound or site is visible through the dressing. The dressing may be left in place for several days if necessary and then removed without disturbing the healing wound or site.

In use as an incise drape the dressing is removed from the pouch, the silicone coated release paper removed and the adhesive adhered to the skin.

An incision may be made through the drape and the drape removed at the end of the operation. Alternatively at the end of the operation a second drape may be placed over the first drape whereby both drapes may remain in place for one to several days if necessary.

Samples of the dressing material prepared as above were taken and the moisture vapour transmission rate measured on (a) a sample in which the adhesive was in contact with moisture vapour but not water and (b) a sample in which the adhesive was in contact with water and not with moisture vapour. The results were 1427 $gm^{-2} 24h^{-1}$ at 37° C. and 100% to 10% relative humidity difference and greater than 14000 $gm^{-2} 24h^{-1}$ at 37° C., respectively.

The resulting laminate is cut into pieces 10 cm×10 cm which are suitable for use as I.V. or wound dressings. The pieces may be placed and then sealed into bacteria-proof and water proof pouches and sterilised by irradiation.

Samples of the material prepared as above were taken and the moisture vapour transmission rate measured on (a) a sample in which the adhesive was in contact with moisture vapour but not water and (b) a sample in which the adhesive was in contact with water and not with moisture vapour. The results were 1472 $gm^{-2} 24h^{-1}$ at 37° C. and 100% to 10% relative humidity difference and 12020 $gm^{-2} 24h^{-1}$ at 37° C.

EXAMPLE 2

A dressing was prepared in a similar manner to that described in Example 1 except that the adhesive layer contained dispersed in it 2% by weight of the adhesive of chlorhexidine dihydrochloride. When tested the dressing showed bactericidally effective release of the antibacterial agent.

EXAMPLE 3

A wound dressing was prepared in a similar manner to that described in Example 1 except that the adhesive layer contained dispersed in its upper surface 0.2% by weight of the adhesive of polyhexamethylene biguanide hydrochloride.

EXAMPLE 4

An adhesive was formed in a similar manner to that described in Example 1 except that hydroabietyl alcohol was added to react with the remaining isocyanate groups after addition of 2-hydroxyethyl methacrylate.

A wound or IV dressing was prepared by laminating a layer of a hydrophilic polyurethane having a weight per unit area of 30 gsm onto a layer of the pressure sensitive adhesive which had been cast onto the release surface of a silicone coated release paper. The adhesive had a weight per unit area of 75 gsm

EXAMPLE 5

An incise drape was prepared by transfer coating a layer of a hydrophilic polyurethane having a weight per unit area of 42 gsm onto a layer of a pressure sensitive adhesive prepared as described in Example 4 at a weight per unit area of 70 gsm) which had been cast onto a silicone coated release paper.

The resulting laminate is cut into pieces which are 20×30cm which are suitable for use as incise drapes. The pieces may be placed and then sealed into bacteria-proof and water proof pouches and sterilised by irradiation.

Samples of the drape material prepared as above were taken and the moisture vapour transmission rate measured on (a) a sample in which the adhesive was in contact with moisture vapour but not water and (b) a sample in which the adhesive was in contact with water and not with moisture vapour. The results were 1200 $gm^{-2} 24h^{-1}$ at 37° C. and 100% to 10% relative humidity difference and 10500 $gm^{-2} 24 h^{-1}$ at 37° C.

EXAMPLE 6

An incise drape as in Example 5 is prepared using a backing at 30 gsm and adhesive at 40 gsm.

The upright and inverted MVTR of this material was determined at 37° C. and 100% to 10% relative humidity difference and found to be 1642 $gm^{-2} 24h^{-1}$ and greater 18000 $gm^{-2} 24h^{-1}$ respectively.

EXAMPLE 7

A polyether-polyamide polymer (Pebax 4011 RN00) film 25 μm thick was laminated onto a film of pressure sensitive adhesive prepared as described in Example 1 which had a weight per unit area of 70 gsm. The adhesive layer is formed by casting or spreading the adhesive onto a silicone-coated release paper. The resulting laminate is cut into pieces which are 10 cm ×10 cm. The pieces may be individually packed and sealed into bacteria-proof and water proof pouches and sterilised by ethylene oxide.

EXAMPLE 8

A film of a blend of polyurethane and high impact polystyrene prepared by the method described in United Kingdom Patent No. 2081721B was laminated to a film of pressure sensitive adhesive prepared as described in Example 1. The thickness of the polymer blend film was 80 μm and the adhesive layer had a weight per unit area of 170 gsm The adhesive layer was prepared by casting onto the release surface of a silicone-coated release paper. The resulting laminate was cut into pieces 10 cm ×10 cm and 5 cm ×8 cm and 10 cm ×20 cm. The pieces were packed and sealed into bacteria-proof and waterproof pouches and sterilised by ethylene oxide.

The upright and inverted MVTRs of samples of the material prepared above were determined at 37° C. and 100% to 10% relative humidity difference and were found to be 1710 $gm^{-2} 24h^{-1}$ and 13, 600 $gm^{-2} 24h^{-1}$.

The thin film dressings of the invention have little or no tendency to self adhere - this feature may be characterised and quantified by the fact that the dressings have less adherence to themselves than to stainless steel. The tests for adhesion to self and to stainless steel were as follows.

Adhesion to Steel

The test method is essentially that described in the British Pharmacopoeia 1980 Edition pp 926. The rectangular stainless steel plates of appropriate size should conform to specification EN 58D of BS 1449. The plates are cleaned before use with acetone, water and toluene vapour bath, followed by cooling and conditioning at 20° C. Strips having a width of 25 mms and a length of about 200 mms are cut from the sample. Immediately before test the release paper is removed and the strip is carefully placed centrally along the length of the plate. A standard 2 Kg roller is passed three times along the strip. The plate is gripped by the lower join of a tensile testing machined. A short length of the test strip is peeled back through 180° C. so that it can be attached to a tab fastened in the upper jaws. Five minutes after rolling, the sample is peeled at 300 mms/min. The results are expressed as average peel force per unit width of sample (Newtons per meter - $Nm^{-1}$).

Adhesion to Self

Two pieces each measuring about 200×30mms are cut from the sample. The release paper is removed from one piece which is placed adhesive side up on a clean flat surface. One end is mashed off with a 10–20 mms tab of single sided release paper, taking care that it is the adherent side of the paper which is contacted with the adhesive. The release paper is now removed from the second piece, which is carefully placed adhesive side down on the first piece so forming a bubble-free adhesive—adhesive bond. A template is lightly rested on the test sample so that a 25 mm strip can be cut from the composite. A standard 2 Kg roller is passed three times along the strip. A further tab of single sided release paper is inserted at the tabbed end to form a symmetrical construction whereby the two release coated sides are in contact. This allows easy separation and insertion of one into the upper jaw and the other into the lower jaw of a tensile testing machine. Five minutes after rolling, the sample is peeled at 300 mm/min. The angle is 90° as the unpeeled portion assumes a horizontal position at the point of separation. The results are expressed as average peel force per unit width of sample (Newtons per meter—$Nm^{-1}$).

In absolute terms, the peel adhesion to self, using the above list may aptly be less than 70 $Nm^{-1}$, more aptly less than 50 $Nm^{-1}$. Preferred dressings have a peel adhesion to self of less than 20 $Nm^{-1}$ and more preferably less than 10 $Nm^{-1}$.

The adherence properties of the dressings of the present invention are illustrated in the following examples.

EXAMPLE 9

A number of adhesives were prepared by mixing together polyoxyethylene—polyoxypropylene diol monobutyl ether, which has a ratio of polyoxyethylene to polyoxypropylene residues of 1:1 and molecular weight of 4095 (300 g, 0.073 moles based on OH value) and a polymeric methylene diphenyl diisocyanate (37.21g, 0.266 moles, —NCO functionality of 2.7) at an NCO/OH ratio of 2.5 in a 700 $cm^3$ flange flask fitted with an overhead stirrer. The flask was heated in a water bath set to a temperature of 90° C. A catalyst comprising dibutyl tin dilaurate (0.2% w/w) was added. The mixture was stirred at 90° C. for two hours The prepolymer so formed was allowed to cool. The prepolymer was a golden yello viscous liquid which may be stored in a capped bottle until ready for use. The prepolymer was found to have an isocyanate content of 1.98%.

Portions A - G of the prepolymer and calculated quantities of polypropylene glycol 2025 and Arbitol which would react with all the available isocyanate were mixed at room temperature until homogenous and then spread onto a silicone release paper at a weight per unit area of 280 gsm and cured at 90° C. to give an adhesive mass. The ratios of polypropylene glycol and arbitol are given in Table 1.

The adhesive masses contained 85% by weight of water when fully hydrated.

Portions of each adhesive were laminated to a 'Melinex' film to form a dressing. The thickness of the film was 25 μm and the adhesive was laminated to a thickness of 50 μm. Each of the dressings was subjected to peel adhesion tests to both self and stainless steel as described above, and the results are shown in Table 1.

TABLE 1

| Adhesion | PPG/Arbitol | Peel from Steel | Peel from Self |
|---|---|---|---|
| A | 100:0 | 18 | 3.4 |
| B | 95:5 | 17 | 5.2 |
| C | 90:10 | 13 | 3.7 |
| D | 85:15 | 22 | 4.5 |
| E | 80:20 | 18 | 5.0 |
| F | 75:25 | 24 | 7.7 |
| G | 70:30 | 39 | 14.6 |

EXAMPLE 10

Adesive thin film dressings were made in a similar manner to that described in Example 9 except the polypropylene glycol was replaced by an ethylene oxide—propylene oxide—ethylene oxide copolymer sold by Dow Chemicals under the trade name Dowfax 63N10. The results of peel test for dressings made from adhesives H to N reported in Table 2.

TABLE 2

| Adhesive | Dowfax/Arbitol | Peel from Steel | Peel from Self |
|---|---|---|---|
| H | 100:0 | 13 | 2.0 |
| I | 95:5 | 13 | 3.4 |
| J | 90:10 | 28 | 5.3 |
| K | 85:15 | 28 | 4.3 |
| L | 80:20 | 43 | 15.5 |
| M | 75:25 | 54 | 13.4 |
| N | 70:30 | 54 | 35.1 |

EXAMPLE 11

In this example peel test results are compared for a dressing in accordance with the invention which is suitable for use as a surgical incise with commercially available incise drapes.

The dressing in accordance with the invention was that of Example 1 except that the adhesive weight on the filmic backing was 51 gm $m^{-2}$. The commercially available drapes were "Tegaderm" and "Tegarderm Plus", manufactured by Minnesota Manufacturing and Thining Company Inc. and "OpSite" (Registered Trade Mark) manufactured by Smith and Nephew Medical Ltd. in which the adhesive-weights were of the order of 30 gm m$^{-2}$. The results of the peel adhesion tests are shown below.

| Dressing | Peel from Steel | Peel from Self |
|---|---|---|
| Example 1 | 25 | 4.4 |
| Tegaderm | 175 | 135. |
| Tegaderm Plus | 181 | 140 |
| "OpSite" | 232 | 330 |

We claim:

1. A thin film wound dressing which comprises a backing layer having over one surface thereof a continuous adhesive layer, which adhesive comprises a gel adhesive which is not self-adherent and which may be removed from the skin without damage thereto, wherein the dressing has a moisture vapour transmission rate of at least 300 gm$^{-2}$ hr$^{-2}$ at 37° C. and 100 to 10% relative humidity difference when in contact with moisture vapour and wherein the content of water leachable materials from the adhesive is less than 10%.

2. A dressing according to claim 1 in which the adhesive is an inherently tacky polyurethane gel adhesive.

3. A dressing according to claim 2 in which the adhesive comprises residues derived from a polyurethane, and an acrylate or methacrylate.

4. A dressing according to claim 1 in which the adhesive is a pressure sensitive adhesive.

5. A dressing according to claim 2 in which the polyurethane gel contains from 35 to 95% by weight of water when hydrated.

6. A dressing according to claim 1 in which the thickness of the adhesive layer is from 0.5 to 5 mm.

7. A dressing according to claim 1 in which the thickness of the adhesive layer is from 10 to 100 μm.

8. A dressing according to claim 1 in which the dressing has a moisture vapour transmission rate of not greater than 2000 gm$^{-2}$ 24h$^{-1}$ at 37° C. and 100% to 10% relative humidity difference.

9. A dressing according to claim 1 in which the dressing has a moisture vapour transmission rate of not less than 2500 gm$^{-2}$ 24h$^{-1}$ at 37° C. when the adhesive is in contact with water.

10. A dressing according to claim 1 wherein the content of water leachable materials from the adhesive is below 5%.

11. A dressing according to claim 1 in which the backing layer comprises a hydrophilic polyurethane which contains from 5 to 50% by weight of water when hydrated and has a thickness when present in the dressing of 15 to 80 μm.

12. A dressing according to claim 1 in which the adhesive layer contains a medicament.

13. A dressing according to claim 12 in which the adhesive contains from 0.1 to 10% of an antibacterial agent.

14. A dressing according to claim 1 which is sterile and is packaged in a bacteria proof and waterproof pouch.

15. A method of treating a wound which comprises applying to the wound a dressing which comprises a backing layer having over one surface thereof a continuous adhesive layer, which adhesive comprises a gel adhesive which is not self-adherent and which may be removed from the skin without damage thereto, wherein the dressing has a moisture vapour transmission rate of at least 300 gm$^{-2}$ hr$^{-1}$ at 37° C. and 100 to 10% relative humidity difference when in contact with moisture vapour and wherein the content of water leachable materials from the adhesive is less than 10%.

16. A method of treating a cavernous wound which comprises filling into the wound cavity an absorbent material and then applying over the wound a dressing which comprises a backing layer having over one surface thereof a continuous adhesive layer which adhesive comprises a gel adhesive which is not self-adherent and which may be removed from the skin without damage thereto, wherein the dressing has a moisture vapour transmission rate of at least 300 gm$^{-2}$ hr$^{-1}$ at 37° C. and 100 to 10% relative humidity difference when in contact with moisture vapour and wherein the content of water leachable materials from the adhesive is less than 10%.

17. A surgical incise drape which comprises a backing layer coated over the operative area thereof with an adhesive layer which comprises a gel adhesive which is not self-adherent and which may be removed from the skin without damage thereto, wherein the drape has a moisture vapour transmission rate of at least 300 gm$^{-2}$ hr$^{-1}$ at 37° C. and 100 to 10% relative humidity difference when in contact with moisture vapour and wherein the content of water leachable materials from the adhesive is less than 10%.

18. A drape according to claim 17 which is sterile and which is packaged in a bacteria-proof pouch.

19. A dressing for covering cannulae sites which comprises a transparent film having upon substantially the whole of one surface thereof a continuous layer of transparent adhesive which comprises a gel adhesive which is not self-adherent and which may be removed from the skin without damage thereto, wherein the dressing has a moisture vapour transmission rate of at least 300 gm$^{-2}$ hr$^{-1}$ at 37° C. and 100 to 10% relative humidity difference when in contact with moisture vapour and wherein the content of water leachable materials from the adhesive is less than 10%.

20. A method of retaining a cannula on the skin at a cannula site which method comprises covering the site with a transparent film having upon substantially the whole of one surface thereof a continuous layer of transparent adhesive which comprises a gel adhesive which is not self-adherent and which may be removed from the skin without damage thereto, wherein the film and adhesive has a moisture vapour transmission rate of at least 300 gm$^{-2}$ hr$^{-1}$ at 37° C. and 100 to 10% relative humidity difference when in contact with moisture vapour and wherein the content of water leachable materials from the adhesive is less than 10%.

21. A method according to claim 15 in which the dressing has a moisture vapour transmission rate of not greater than 2000 gm$^{-2}$ 24h$^{-1}$ at 37° C. and 100 to 10% relative humidity difference.

22. A method according to claim 15 wherein the content of water leachable materials from the adhesive is below 5%.

23. A method according to claim 16 in which the dressing has a moisture vapour transmission rate of not greater than 2000 gm$^{-2}$ 24h$^{-1}$ at 37° C. and 100 to 10% relative humidity difference.

24. A method according to claim 16 wherein the content of water leachable materials from the adhesive is below 5%.

25. A drape according to claim 17 in which the drape has a moisture vapour transmission rate of not greater than 2000 gm$^{-2}$ 24h$^{-1}$ at 37° C. and 100 to 10% relative humidity difference.

26. A drape according to claim 17 wherein the content of water leachable materials from the adhesive is below 5%.

27. A dressing according to claim 19 in which the dressing has a moisture vapour transmission rate of not greater than 2000 gm$^{-2}$ 24h$^{-1}$ at 37° C. and 100 to 10% relative humidity difference.

28. A dressing according to claim 19 wherein the content of water leachable materials from the adhesive is below 5%.

29. A method according to claim 20 in which the film and adhesive has a moisture vapour transmission rate of not greater than 2000 gm$^{-2}$ 24h$^{-1}$ at 37° C. and 100 to 10% relative humidity difference.

30. A method according to claim 20 wherein the content of water leachable materials from the adhesive is below 5%.

* * * * *

UNITED STATES PATENT AND TRADEMARK OFFICE
CERTIFICATE OF CORRECTION

PATENT NO. : 5,183,664
DATED : February 2, 1993
INVENTOR(S) : Christopher Wilson Guy Ansell, et al.

It is certified that error appears in the above-indentified patent and that said Letters Patent is hereby corrected as shown below:

IN THE ABSTRACT:

Penultimate line, change "$hr^{-1}$" to — $24\ hr^{-1}$ —.

Column 2, line 60, change "$hr^{-1}$" to — $24\ hr^{-1}$ —.

IN THE CLAIMS:
Col. 15:
Claim 1, line 7, change "$hr^{-2}$" to — $24\ hr^{-1}$ —.

Claim 15, line 8, change "$hr^{-1}$" to — $24\ hr^{-1}$ —.
Col. 16:
Claim 16, fifth to last line, change "$hr^{-1}$" to — $24\ hr^{-1}$ —.

Claim 17, fourth to last line, change "$hr^{-1}$" to — $24\ hr^{-1}$ —.

Claim 19, fourth to last line, change "$hr^{-1}$" to — $24\ hr^{-1}$ —.

Claim 20, fourth to last line, change "$hr^{-1}$" to — $24\ hr^{-1}$ —.

Signed and Sealed this

Sixth Day of December, 1994

Attest:

BRUCE LEHMAN

Attesting Officer    Commissioner of Patents and Trademarks